US009468711B2

(12) United States Patent
Iwase et al.

(10) Patent No.: US 9,468,711 B2
(45) Date of Patent: Oct. 18, 2016

(54) SYRINGE STORAGE CONTAINER

(71) Applicant: Terumo Kabushiki Kaisha, Tokyo (JP)

(72) Inventors: Yoichiro Iwase, Yamanashi (JP);
Junichi Ogawa, Yamanashi (JP);
Kouichi Tachikawa, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/582,907

(22) Filed: Dec. 24, 2014

(65) Prior Publication Data
US 2015/0108020 A1 Apr. 23, 2015

Related U.S. Application Data

(63) Continuation of application No. PCT/JP2012/066246, filed on Jun. 26, 2012.

(51) Int. Cl.
*A61M 5/00* (2006.01)
*A61M 5/31* (2006.01)
*A61M 5/34* (2006.01)

(52) U.S. Cl.
CPC .............. *A61M 5/002* (2013.01); *A61M 5/008* (2013.01); *A61M 5/3134* (2013.01); *A61M 5/344* (2013.01); *A61M 5/347* (2013.01); *A61M 2005/3104* (2013.01)

(58) Field of Classification Search
CPC .. A61M 5/002; A61M 5/008; A61M 5/3134; A61M 5/3205; A61M 5/347; A61M 2005/3104; A61M 5/32; A61B 19/02; B65D 25/10
USPC .......... 206/366, 443, 364, 365; 211/60.1, 74
See application file for complete search history.

(56) References Cited

U.S. PATENT DOCUMENTS

| 4,142,633 A * | 3/1979 | Raghavachari ....... A61M 5/008 206/366 |
| 5,024,616 A * | 6/1991 | Ogle, II .............. A61M 5/3271 604/192 |
| 7,104,400 B2 * | 9/2006 | Kiehne ............... A61M 5/3205 206/366 |
| 8,118,167 B2 * | 2/2012 | Togashi ............... A61M 5/008 206/519 |

(Continued)

FOREIGN PATENT DOCUMENTS

| GB | WO 2011110872 A1 * | 9/2011 | ......... A61B 19/0256 |
| JP | 2001-327577 A | 11/2001 | |

(Continued)

OTHER PUBLICATIONS

International Search Report dated Aug. 28, 2012 issued in Application No. PCT/JP2012/066246.

*Primary Examiner* — Bryon Gehman
(74) *Attorney, Agent, or Firm* — Foley & Lardner LLP

(57) ABSTRACT

A syringe container includes a cylindrical syringe including a distal end portion having a discharge opening for discharging a liquid, a proximal end portion, and a side peripheral section connected to the distal end portion and the proximal end portion; an attachment member configured to be attached to the distal end portion and having an outer radius larger than an outer radius of the side peripheral section; a container body including a bottom portion and a peripheral wall portion extending upward from a periphery of the bottom portion; and a syringe holding section configured to be placed within the peripheral wall portion so as to face the bottom portion.

15 Claims, 5 Drawing Sheets

(56) References Cited

U.S. PATENT DOCUMENTS

| | | | |
|---|---|---|---|
| 8,485,357 B2 * | 7/2013 | Song | A61M 5/008 206/366 |
| 9,095,667 B2 * | 8/2015 | Von Schuckmann | A61M 5/5086 |
| 2001/0052476 A1 | 12/2001 | Heinz et al. | |
| 2010/0012546 A1 | 1/2010 | Togashi et al. | |
| 2012/0118777 A1 * | 5/2012 | Kakiuchi | A61M 5/002 206/366 |
| 2013/0001117 A1 * | 1/2013 | Liversidge | A61B 19/0256 206/364 |
| 2014/0358078 A1 * | 12/2014 | Fischer | A61M 5/3134 604/111 |

FOREIGN PATENT DOCUMENTS

| | | | | |
|---|---|---|---|---|
| JP | 2006-508700 A | 3/2006 | | |
| JP | 4685198 B1 | 5/2011 | | |
| JP | 2011-160875 | 8/2011 | | |
| JP | 2012-100927 | 5/2012 | | |
| JP | WO 2013146296 A1 * | 10/2013 | | A61M 5/344 |
| WO | WO-03/080467 A1 | 10/2003 | | |
| WO | WO-2008/107961 A1 | 9/2008 | | |

\* cited by examiner

SYRINGE STORAGE CONTAINER

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/066246 filed on Jun. 26, 2012, the entire contents of which is hereby incorporated by reference in its entirety.

BACKGROUND

1. Technical Field

The present disclosure relates to a syringe container for containing a plurality of syringes.

2. Background Art

Conventionally, a syringe container that can hold a plurality of syringes upright is used when transporting or storing syringes before the syringes are filled with liquid medicines. Such a syringe container is configured with a box-shaped container body with an opened top and a syringe holding section that can hold a plurality of syringes upright. Inside the container body, a ledge-like section is provided to support the syringe holding section. The syringe holding section is configured with a plate-like member having a plurality of through-holes. The syringe is inserted in the through-hole and the flange section provided on the end portion of the syringe is placed on the rim of the through-hole. The syringe is thereby held in the syringe holding section. Using such a syringe container, a plurality of syringes can be held upright with filling ports for liquid medicine of the syringes facing upward.

Generally, if syringes and liquid medicines are produced by different companies, the syringe container is produced by the company producing syringes and shipped to the company producing liquid medicines. Liquid medicines are filled in syringes in the company producing liquid medicines. The company manufacturing syringes can use the aforementioned syringe container to store and transport a plurality of syringes at the same time. The company producing liquid medicines can simply take out the syringe holding section holding a plurality of syringes from the container and set them in an apparatus for filling liquid medicines. This makes the operation of filling liquid medicines into syringes efficient.

Such a known container is discussed in WO 2008/107961 A. The medical container discussed in WO 2008/107961 A includes a box-like container body with an opened top, a plate-like holding unit provided inside the container body, and a plurality of cylindrical holding sections formed in the holding unit.

When containing an injection sleeve with a cap thereon in the medical container, the flange section of the injection cylinder abuts the holding unit as the injection cylinder advances in the sleeve hole of the holding unit. The injection cylinder is thus held in the holding unit and contained in the container body.

A conventional syringe including a Luer lock that connects the distal end of a syringe (injection cylinder) and a cap (nozzle cap) or a needle holding member that holds an injection needle and a thread is known. When a cap to be attached to a Luer-lock syringe having a small diameter and a small injection volume, for example, 0.5 milliliters (ml), is formed with an outer diameter equal to the outer diameter of the syringe body, the cap diameter also becomes small, which makes it difficult to rotate the cap to remove.

To solve such problem, the cap can be formed with an outer diameter larger than the outer diameter of the syringe body.

If a syringe attached with a cap having an outer diameter larger than the outer diameter of the syringe body is contained in the medical container discussed in WO 2008/107961 A, the difference between the diameter of the sleeve hole of the holding unit and the outer diameter of the cap becomes small.

As for a typical medicine, particularly for protein preparations such as vaccines, the protein preparation is filled in the syringe contained in the medical container. The syringe is checked for shipping and then transferred to a packing line. Since the preparation cannot be stored under room temperature, the preparation is generally stored in a refrigerator until checked for shipping. In order to efficiently transfer the syringes filled with medicine to the packing line and to efficiently store the syringes in the refrigerator, the syringes are lined up in one direction in a rondo tray and stacked to be stored. To line up the syringes in the rondo tray, the syringes are quickly pulled out vertically by an automatic holding unit pull-out machine.

When the degree of shift between the center axis of the syringe held in the holding unit and the center axis of the sleeve hole is large, the cap may abut the inner rim of the holding section forming the through-hole when the syringe is pulled out. When the syringe is further pulled out with the cap abutting the holding section, the holding unit may rise with the syringe.

Then when the holding unit and the cap make relative motions and release each other, the holding unit falls and makes vibration which might cause other syringes held in the holding unit to come out of the sleeve hole of the holding section. When a syringe comes out of the sleeve hole of the holding section, the liquid filled in the syringe may spill out of the syringe or the syringe may be damaged.

SUMMARY OF INVENTION

In light of the foregoing, one object of the present invention is to provide a syringe container that allows a syringe to be pulled out without raising the syringe holding section.

According to one embodiment, a syringe container includes a syringe, an attachment member, a container body, and a syringe holding section.

In one aspect, the cylindrically formed syringe includes a distal end portion with a discharge opening for discharging the filled liquid, a proximal end portion located opposite to the distal end portion, and a side peripheral section connected to the distal end portion and the proximal end portion. The attachment member is attached to the distal end portion and has an outer radius larger than an outer radius of the side peripheral section.

In one aspect, the container body includes a bottom portion located at the bottom end and a peripheral wall portion continuously extending upward from the periphery of the bottom portion. The syringe holding section is placed within the peripheral wall portion to face the bottom portion and has a through-hole in which the syringe is vertically inserted, and holds the syringe by inserting the syringe in the through-hole. Further, a peripheral surface forming the through-hole has an upper end of which radius is larger than the outer radius of the attachment member, a bottom end of which radius is larger than the radius of the upper end, and a tapered section having a diameter reducing as the tapered section extends upward from the bottom end.

In the syringe container thus configured, the peripheral surface forming the through-hole of the syringe holder has a tapered section. The diameter of the tapered section reduces as the tapered section extends upward from the bottom end of the peripheral surface.

Accordingly, when the syringe attached with the attachment member and held in the syringe holding section is to be pulled out from the through-hole, if the degree of the shift between the center axis of the syringe and the center axis of the through-hole is large, the attachment member or the distal end portion of the syringe attached with the attachment member makes contact with the tapered section. As the attachment member or the distal end portion of the syringe slides upward along the tapered surface of the tapered section, the degree of shift between the center axis of the syringe and the center axis of the through-hole decreases. This prevents the attachment member or the distal end portion of the syringe from abutting the outer rim of the through-hole of the syringe holding section. The syringe can thus be pulled out without raising the syringe holding section.

DETAILED DESCRIPTION

Figure 1:
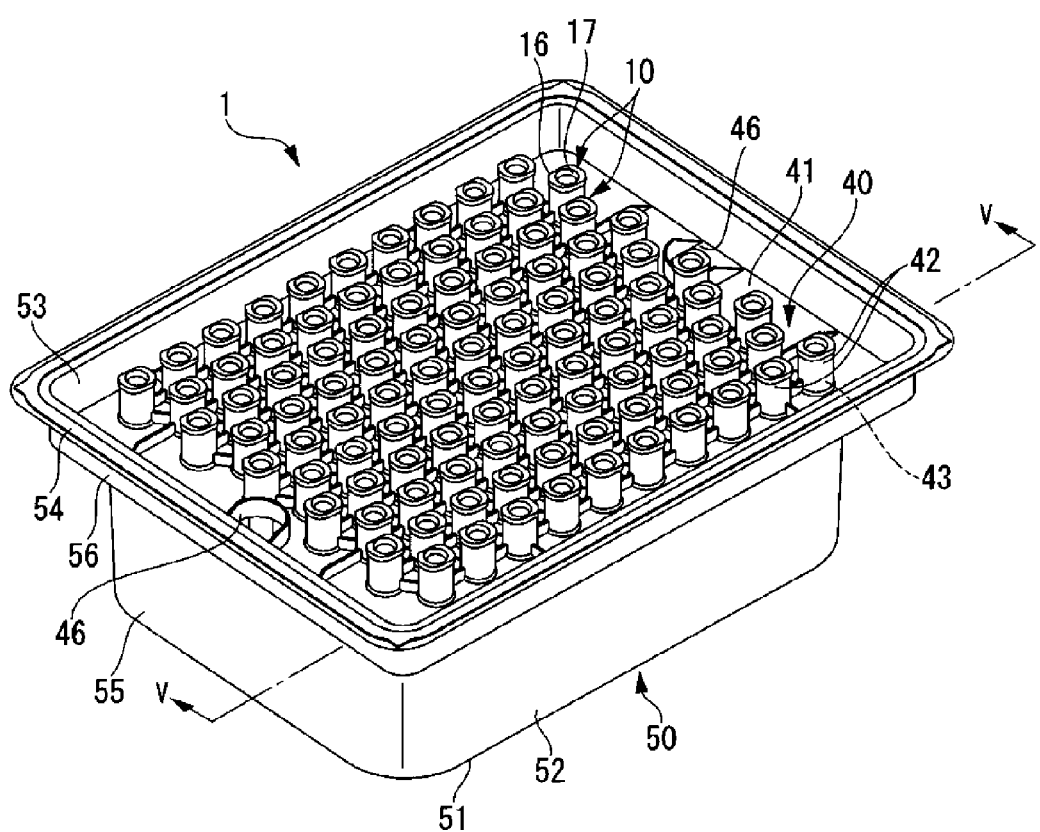
FIG. 1 is a perspective view of a syringe container according to an embodiment of the present invention.

A syringe container according to an embodiment of the present invention will be described below referring to FIGS. 1 to 5. The same component is appended with the same reference sign in the drawings. The present invention is not limited to the embodiment described below.
Configuration of Syringe Container A configuration of a syringe container 1 of the embodiment will be described referring to FIG. 1. FIG. 1 is the perspective view of the syringe container 1 of the embodiment.

The syringe container 1 of the embodiment is used to transfer and store a plurality of syringes 10 at the same time. As illustrated in FIG. 1, the syringe container 1 is configured with a container body 50 formed in an approximately square-box-shape, a syringe holding section 40 placed within the container body 50, a syringe 10 held in the syringe holding section 40, and a cap 30 (see FIGS. 2A to 2C) attached to the syringe 10. The syringe 10 with a cap 30 attached to the distal end portion thereof is inserted in a through-hole 43 formed in the syringe holding section 40 to be held in the syringe holding section 40.

The syringe 10 and the cap 30 of the embodiment will be described referring to FIGS. 2A to 3.

Figure 2A:
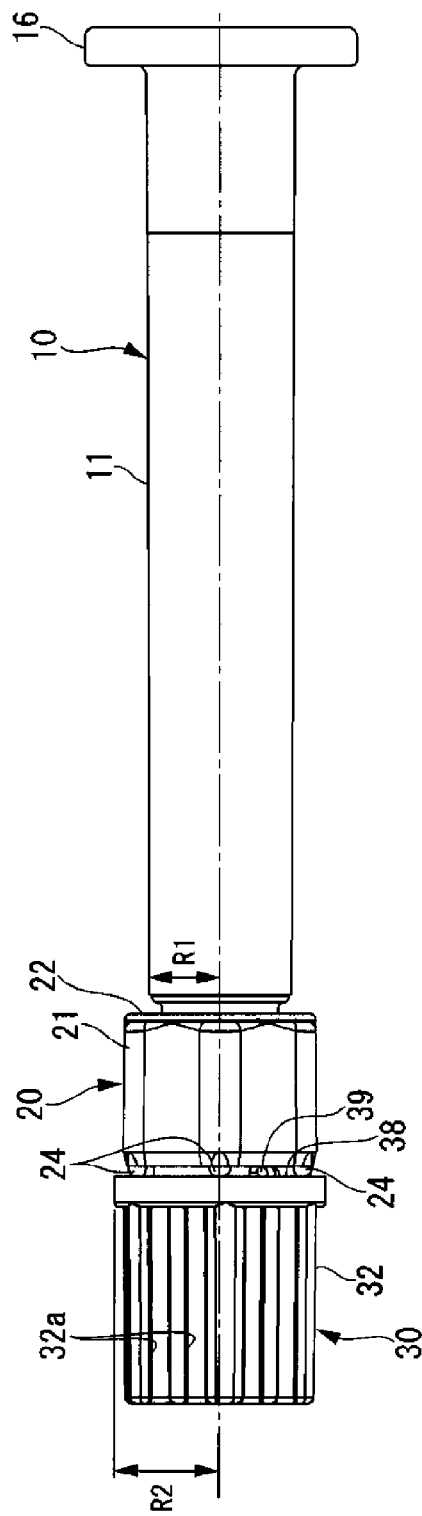
FIG. 2A is a side view of the syringe in FIG. 1 with a cap attached.
Figure 2C:
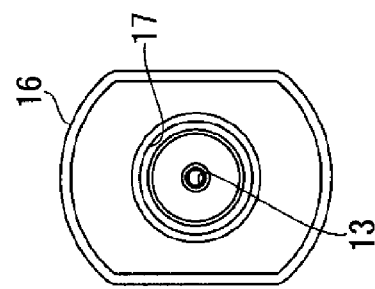
FIG. 2C is a rear view of the syringe in FIG. 1 with the cap attached.
Figure 2B:
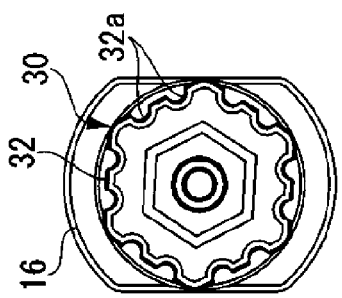
FIG. 2B is a front view of the syringe in FIG. 1 with the cap attached.
Figure 3:
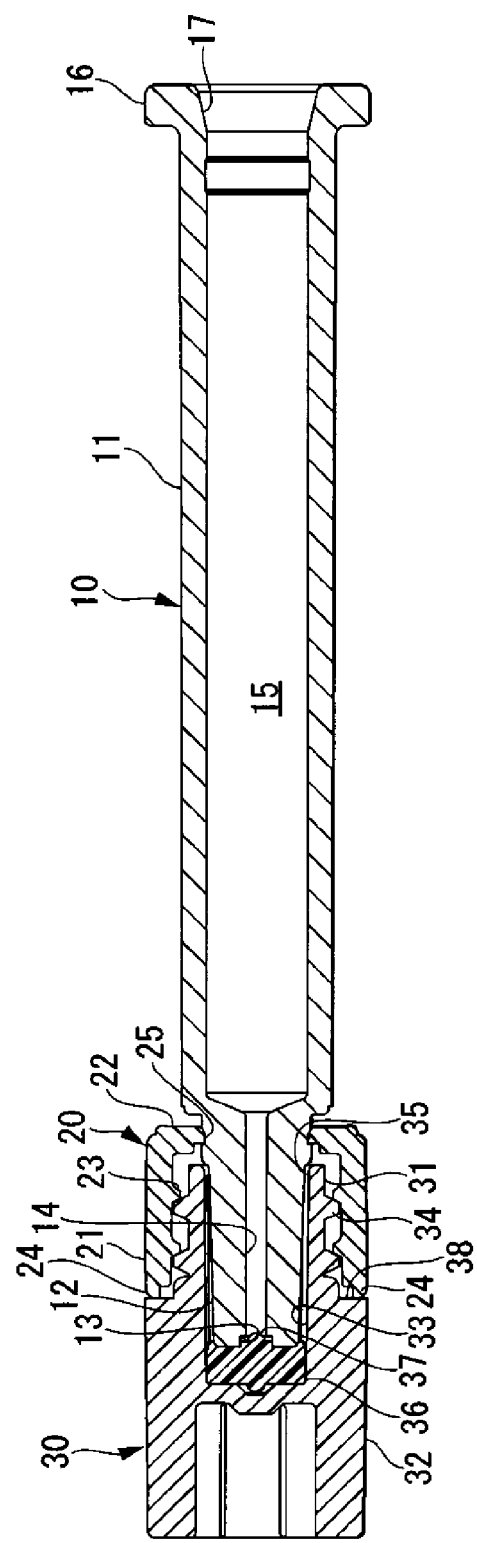
FIG. 3 is a sectional view of the syringe in FIG. 1 with the cap attached.

FIGS. 2A to 3 illustrate the syringe 10 attached with the cap 30 according to the embodiment.
Syringe As illustrated in FIGS. 2A to 3, the syringe 10 of the embodiment is formed in an approximately cylindrical shape. With the distal end of the syringe 10 plugged with the cap 30, the sleeve hole of the syringe 10 is filled with liquid such as a liquid medicine.

The syringe 10 includes an approximately cylindrically formed side peripheral section 11, a discharge section (distal end portion) 12 (see FIG. 3) formed on a first end of the side peripheral section 11, and a flange section (proximal end portion) 16 formed on a second end of the side peripheral section 11.

The side peripheral section 11 is integrally formed with the discharge section 12 and the flange section 16. That is, the side peripheral section 11 continues to the discharge section 12 and the flange section 16. A liquid chamber 15 for storing the filled liquid medicine is formed inside the side peripheral section 11.

The outer radius R1 (see FIGS. 2A to 2C) of the side peripheral section 11 can suitably be determined according to applications and the amount of liquid medicine stored in the liquid chamber 15. For example, when the amount of liquid medicine is 0.5 ml, the outer radius R1 of the side peripheral section 11 is preferably within a range from 3.4 to 4.1 mm. For example, when the amount of liquid medicine is 1 ml, the outer radius R1 of the side peripheral section 11 is preferably within a range from 4.05 to 4.7 mm. In the embodiment, the amount of liquid medicine to be stored in the liquid chamber 15 is 0.5 ml and the outer radius R1 of the side peripheral section 11 is 3.5 mm.

As illustrated in FIG. 3, the discharge section 12 is formed in an approximately cylindrical shape that projects from one of ends of the side peripheral section 11 such that the axis of the discharge section 12 is identical to the center axis of the side peripheral section 11. The outer radius of the discharge section 12 is smaller than the outer radius R1 of the side peripheral section 11. The discharge section 12 is formed in a tapered shape where the outer radius gradually reduces toward the distal end. A discharge opening 13 for discharging a liquid medicine is formed in the distal end portion of the discharge section 12. Further, a discharge passage 14 is formed in the discharge section 12 to communicate with the discharge opening 13 and the liquid chamber 15 of the side peripheral section 11. The liquid medicine stored in the liquid chamber 15 may be discharged through the discharge opening 13.

A Luer-lock portion 20 is provided on the discharge section 12. The Luer-lock portion 20 is an approximately cylindrically shaped member arranged to be concentric with the side peripheral section 11. The Luer-lock portion 20 includes a sleeve portion 21 extending along the center axis and an engagement portion 22 extending inward from a first end portion of the sleeve portion 21.

The outer radius of the sleeve portion 21 is larger than the outer radius R1 of the side peripheral section 11. An internal thread 23 is integrally formed on the inner peripheral surface of the sleeve portion 21. On a second end portion of the sleeve portion 21, a plurality of projections 24 projecting along the center axis is formed. The projections 24 are arranged along the circumferential direction about the center axis, evenly spaced by a predetermined interval.

An engagement hole 25 is formed in the approximately middle portion of the engagement portion 22. The discharge section 12 is inserted in the engagement hole 25 and then the engagement portion 22 engages with the proximal end of the discharge section 12, whereby a Luer-lock portion 20 is attached to the discharge section 12.

The flange section 16 extends radially outward from the second end portion of the side peripheral section 11 and is formed in an approximately oval-shape when viewed from the rear side. A filling port 17 is formed in the approximately middle portion of the flange section 16 and communicates with the liquid chamber 15 of the side peripheral section 11. The filling port 17 is formed in a funnel-shape so that the liquid medicine can easily be filled in the liquid chamber 15. The outer radius of a portion of the flange section 16 is larger than the inner radius of the upper end of the support cylinder 42 forming the through-hole 43 of the syringe holding section 40 which will be described later. Thus, when the syringe 10 is inserted, with the discharge section 12 of the syringe 10 pointing downward, in the through-hole 43 of the syringe holding section 40 from above, the flange section 16 is supported by the support cylinder 42 of the syringe holding section 40 and thereby the syringe 10 is held in the syringe holding section 40. The shape of the flange section 16 is not limited to the oval-shape as in the embodiment and may be, for example, an annular shape.

A resin is used as the material of the syringe 10 in the embodiment, though various types of metal and glass may be used. The Luer-lock portion 20 may be formed integrally with the discharge section 12.

Cap

The cap 30 is formed of an approximately cylindrically shaped resin and includes a small diameter section 31, a large diameter section 32, and a discharge section insertion hole 33.

The small diameter section 31 is provided in a first end of the cap 30 and has an outer radius smaller than the large diameter section 32 provided in a second end of the cap 30. The small diameter section 31 and the large diameter section 32 are integrally formed. An external thread 34 is formed on the outer peripheral surface of the small diameter section 31 which engages with the internal thread formed in the Luer-lock portion 20 of the syringe 10.

The discharge section insertion hole 33 is provided within the cap 30 and extends along the center axis of the cap 30. A first end of the discharge section insertion hole 33 communicates with an aperture 35 provided in a first end of the small diameter section 31 as to be opened to the outside. A second end of the discharge section insertion hole 33 is closed. An approximately cylindrically shaped packing 36 provided as an elastic member (e.g., a rubber) engages with the other end of the discharge section insertion hole 33. A packing projection 37 projecting along the center axis is formed in the approximately middle portion of the packing 36.

A contact face 38, which radially extends inward to the outer periphery of second end of the small diameter section 31, is formed on one of ends of the large diameter section 32. On the contact face 38, a plurality of cap projections 39 (see FIGS. 2A to 2C) projecting along the center axis is formed. The cap projections 39 are arranged along the circumferential direction about the center axis and evenly spaced by a predetermined interval.

A plurality of grooves 32a extending along the center axis is formed on the outer peripheral surface of the large diameter section 32. The grooves are evenly spaced by a predetermined interval. The grooves produce large friction between a finger of a user when the cap 30 is to be removed from the syringe 10. The user can easily rotate the cap 30 in the removal direction.

The outer radius R2 of the large diameter section 32 is larger than that of the Luer-lock portion 20 of the syringe 10 and the outer radius R1 of the side peripheral section 11. Typically, a syringe configured with a cap, a lock, and a packing must secure liquid-tightness under sterilizing procedures, transportation of products, vibration, and dropping of the product until the validated date comes. To secure liquid-tightness, a seal is attached to the cap to prevent loosening, or alternatively, the cap is tightened by a certain degree of torque to push the distal end portion of the discharge section of the syringe into the packing. In such method, considering dimensional tolerances in the production of the cap, the lock, and the packing, the distal end portion of the discharge section has to be pushed into the packing by 0.5 mm or more. When a user wishes to release the liquid-tightness, the user should provide a certain degree of torque to rotate the cap for uncapping. The larger the cap size (outer radius) is, the larger the produced torque is, making it easy to uncap. Among those syringes configured with a cap, a lock, and a packing sold on the market, the smallest size of the cap of the syringe is about 8.0 mm.

As will be described below, the difference between the outer radius R2 of the large diameter section 32 and the outer radius R1 of the side peripheral section 11 is preferably within a range from 1 to 2 mm. Hereinafter, the difference between the outer radius R2 of the large diameter section 32 and the outer radius R1 of the side peripheral section 11 is referred to as syringe radius difference. The outer radius R2 of the large diameter section 32 is 5 mm in the embodiment. That is, the syringe radius difference in the embodiment is 1.5 mm which is the difference between 5 mm, the outer radius R2 of the large diameter section 32, and 3.5 mm, the outer radius R1 of the side peripheral section 11.

By inserting the discharge section 12 in the discharge section insertion hole 33, inserting the small diameter section 31 of the cap 30 in the sleeve hole of the sleeve portion 21 of the Luer-lock portion 20, and rotating the attached cap 30 by a predetermined degree, the external thread 34 of the small diameter section 31 engages with the internal thread 23 of the Luer-lock portion 20. The cap projection 39 first contacts the projection 24 of the sleeve portion 21 and slides over the projection 24 of the sleeve portion 21, and then the contact face 38 of the cap 30 contacts the distal end of the projection 24 of the sleeve portion 21. The cap 30 is thereby connected to the Luer-lock portion 20 and attached to the syringe 10.

The distal end portion of the discharge section 12 of the syringe 10 is then pushed into the packing 36, and thereby the packing projection 37 plugs the discharge opening 13 of the discharge section 12. This prevents the liquid medicine stored in the liquid chamber 15 from leaking outside of the syringe 10 through the discharge passage 14 and the discharge opening 13.

When the cap 30 is attached, the projection 24 of the sleeve portion 21 making contact with the cap projection 39 restricts the cap 30 rotating in the removal direction. If a predetermined degree or greater force is applied to the cap 30 in the removal direction, the cap projection 39 slides over the projection 24 of the sleeve portion 21, and thereby the cap 30 can rotate in the removal direction, in other words, the cap 30 can be removed.

Syringe Holding Section

Figure 4A:
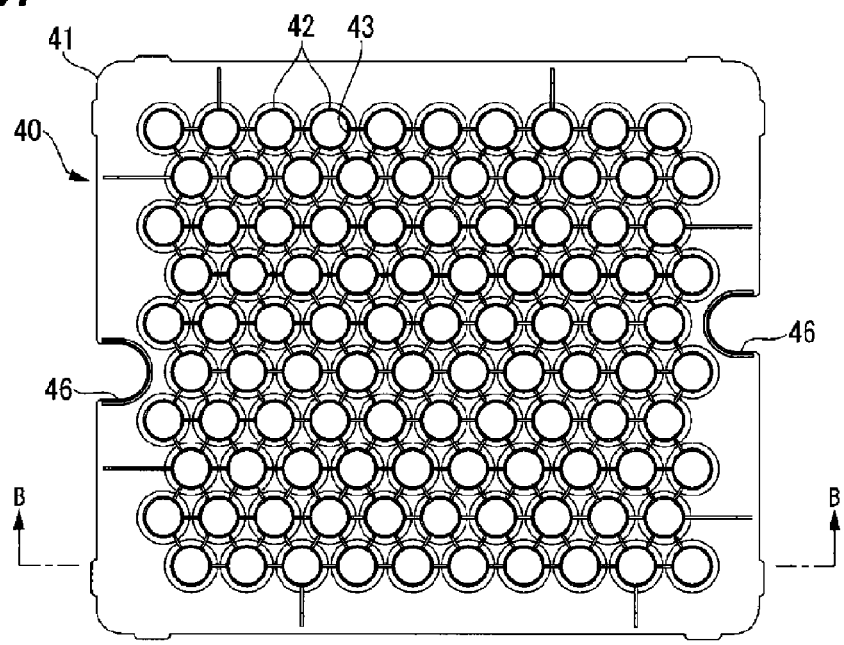
FIG. 4A is a top view of the syringe holding section in FIG. L.
Figure 4B:
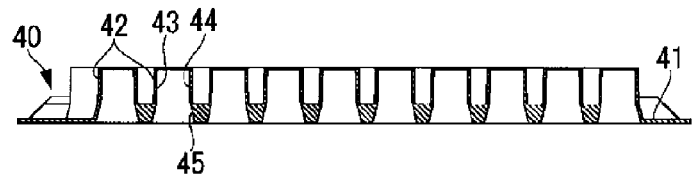
FIG. 4B is a sectional view of the syringe holding section in FIG. 1 taken along the line B-B in FIG. 4A.
Figure 4C:
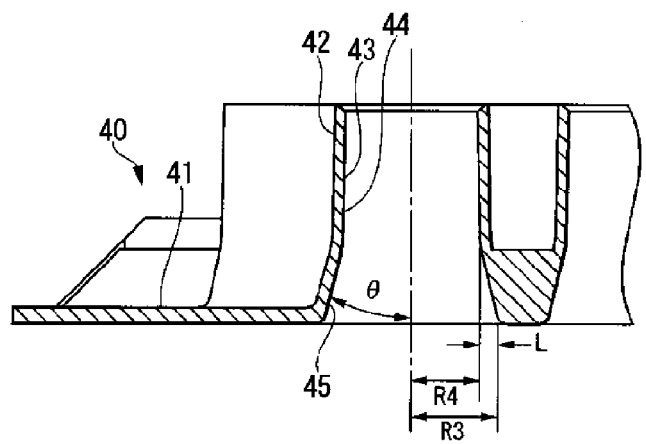
FIG. 4C is an enlarged view of a portion of the syringe holding section illustrated in FIG. 4B.

The syringe holding section 40 will be described referring to FIGS. 4A to 4C. FIGS. 4A to 4C illustrate the syringe holding section 40.

The syringe holding section 40 is a resin member including a square-plate-shaped base plate 41 and a plurality of support cylinders 42 projecting from the top face of the base plate 41. A through-hole 43 penetrating the base plate 41 is formed within the support cylinder 42 to insert the syringe 10 therein.

The inner peripheral surface (peripheral surface) 44 of the support cylinder 42 forming the through-hole 43 has an upper end which has a radius larger than the outer radius R2 of the large diameter section 32 and a bottom end which has a radius larger than the radius of the upper end. The inner peripheral surface 44 has a tapered section 45 from the bottom end to the approximately middle portion of the support cylinder 42 where the radius reduces as the tapered section 45 extends upward. The tapered shape of the tapered section 45 may be a linear taper, an exponential curve taper, or an inverted parabolic curve. In particular, a linear taper is preferably used. From the approximately middle portion to the upper end of the support cylinder 42, the radius of the inner peripheral surface 44 is constant.

As will be described below, the radius R3 of the bottom end of the tapered section 45 and the radius R4 of the upper end of the tapered section 45 are preferably set such that the difference (hereinafter referred to as tapered distance L) is larger than the syringe radius difference. In the embodiment, the radius R3 of the bottom end of the tapered section 45 is 7.5 mm, and the radius R4 of the upper end of the tapered section 45 is 5.865 mm. That is, the tapered distance L in the embodiment is 1.635 mm, which is larger than the syringe radius difference, which is 1.5 mm.

As will be described below, if the syringe radius difference is 1 mm and the tapered distance L is within a range from 1 to 4 mm, the inclination angle of the tapered section 45 to the center axis of the through-hole 43 (hereinafter referred to as taper angle θ) is preferably within a range from 5 to 40 degrees. If the syringe radius difference is 2 mm and the tapered distance L is within a range from 2 to 4 mm, the taper angle θ is preferably within a range from 5 to 30 degrees. The taper angle θ is 13.35 degrees in the embodiment.

A plurality of support cylinders 42 is staggeredly arranged on the base plate 41. The support cylinders 42 are evenly spaced by a predetermined distance. In this manner, the distance between adjacent support cylinders 42 is approximately constant, and thereby the distance between syringes 10 inserted through the support cylinders 42 to be held is approximately constant. This prevents the contact between adjacent syringes 10 caused by vibration or the like during transportation of the syringe container 1.

In each of two opposing sides of the base plate 41, an approximately half-circle-shaped notch 46 is formed. As will be described below, by putting a finger or the like in the notch 46, the syringe holding section 40 can easily be raised, so that the syringe holding section 40 placed within the container body 50 can easily be taken out from the syringe holding section 40.

Container Body

Figure 5:
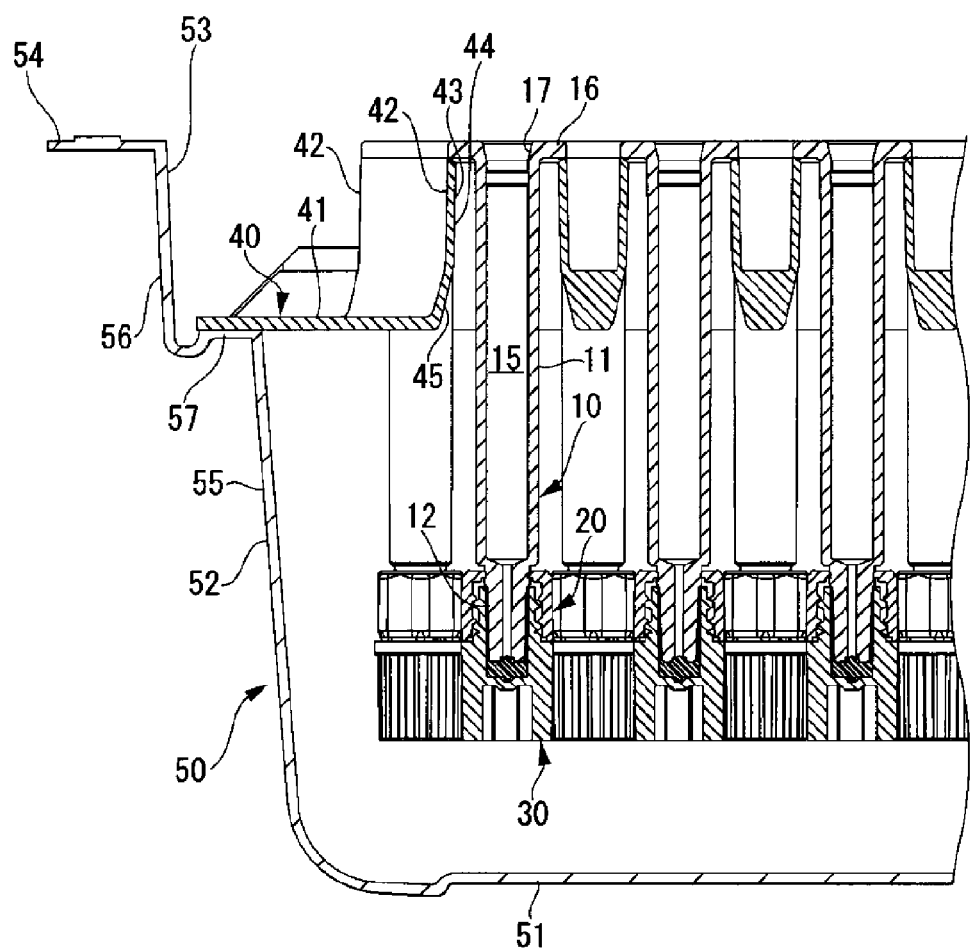
FIG. 5 is a sectional view of the syringe container taken along the line V-V in FIG. 1.

The container body 50 will be described referring to FIG. 5. FIG. 5 is a sectional view of the syringe container 1 taken along the line V-V in FIG. 1.

The container body 50 is a resin member formed in an approximately square-box-shape. As illustrated in FIG. 5, the container body 50 includes an approximately square-plate-like bottom portion 51 and a peripheral wall portion 52 extending upward from the outer periphery of the bottom portion 51. The container body 50 further includes an opening 53 surrounded by the upper end of the peripheral wall portion 52 and a flange 54 surroundingly continuing to the upper end of the peripheral wall portion 52. The internal space of the container body 50 surrounded by the peripheral wall portion 52 and the bottom portion 51 serves as a container space for containing the syringe holding section 40 and the syringe 10.

The peripheral wall portion 52 includes a lower peripheral wall portion 55, an upper peripheral wall portion 56, and a ledge section 57. The lower peripheral wall portion 55 extends upward with an outward inclination from the outer periphery of the bottom portion 51. The ledge section 57 is formed in a frame-shape extending outward of the lower peripheral wall portion 55 from the upper edge of the lower peripheral wall portion 55 so as to be parallel to the bottom portion 51. The upper peripheral wall portion 56 extends upward from the outer periphery of the ledge section 57.

The flange 54 is formed in a frame-shape extending outward from the upper edge of the upper peripheral wall portion 56 so as to be parallel to the bottom portion 51. A film (not shown) to seal the syringe container 1 when shipping the syringe container 1 is attached to the flange 54. As for the film, a moisture permeable and waterproof sheet that is usable under a sterilizing process employing high temperature steam or gas such as high pressure steam sterilization (autoclaving) and EOG (ethylene oxide gas) sterilization is used.

Preferably, the resin used for the syringe 10, the cap 30, the syringe holding section 40, and the container body 50 is such that the property does not change under the sterilization process employing high temperature steam or gas such as high temperature steam sterilization and EOG sterilization. Such resins include resistant resins, for example, polypropylene, polystyrene, polyethylene, polycarbonate, ABS resin, PET, or the like. Further, preferably, the syringe holding section 40 and the container body 50 are substantially transparent or semitransparent to secure visibility of the inside of the container body 50. Such materials, among the aforementioned resins, include polycarbonate, polystyrene, and PET.

Referring to FIG. 5, the state of the syringe container 1 according to the embodiment where the syringe 10 attached with the cap 30 is held in the syringe holding section 40 placed within the container body 50 will be described. FIG. 5 is a sectional view of the syringe container 1 taken along the line V-V in FIG. 1.

As illustrated in FIG. 5, the syringe holding section 40 is inserted in the container body 50 from above to be held therein, and the bottom face of the outer peripheral portion of the base plate 41 of the syringe holding section 40 makes contacts with the top surface of the ledge section 57. That is, the syringe holding section 40 is mounted on the ledge section 57 to be placed within the container body 50. The ledge section 57 restricts the syringe holding section 40 from descending in the container body 50.

The base plate 41 of the syringe holding section 40 faces the bottom portion 51 of the container body 50.

The syringe 10 attached with the cap 30 is inserted in the through-hole 43 of the syringe holding section 40. The syringe holding section 40 holds the syringe 10 by way of the upper end of the support cylinder 42 supporting the flange section 16 of the syringe 10.

Now, the result of the experiment carried out for the syringe container 1 of the embodiment will be described. In the experiment, the abutting of the syringe 10 against the syringe holding section 40 is tested for cases with different values of the taper angle θ, the syringe radius difference, and the tapered distance L. In the experiment, syringe containers 1 corresponding to each combination of the taper angle θ, the syringe radius difference, and the tapered distance L are prepared. For each syringe container 1, the syringe 10 is pulled out from the syringe container 1 to test whether the syringe holding section 40 rises.

Specifically, for this experiment, three types of caps 30 of 1, 2, and 3 mm are used. Further, 20 types of syringe holding sections 40 are used where the tapered distance L has variation of 1, 2, 3, and 4 mm and the tapered angle θ of the tapered section 45 has variation of 5, 10, 30, 40, and 50 degrees.

In the experiment, one syringe 10 attached with a cap 30 is inserted in the through-hole 43 of each syringe holding section 40 fixed to a jig (not shown) with a large degree of shift provided between the center axis of the syringe 10 and the center axis of the through-hole 43. In this manner, when the syringe 10 is pulled up, the Luer-lock portion 20 of the syringe 10 or the cap 30 makes contacts with the tapered section 45 of the inner peripheral surface 44 of the syringe holding section 40.

In this experiment, the syringe 10 inserted in the syringe holding section 40 is pulled upward by a robot arm (not shown) to test whether the syringe 10 or the cap 30 abuts and raises the syringe holding section 40. The speed of pulling up the syringe 10 by the robot arm is set to 500 mm/min. Three tests are performed for each combination of the cap 30 and the syringe holding section 40.

The results of the experiment are shown in Table 1.

be pulled out from the through-hole 43, if the degree of the shift between the center axis of the syringe 10 and the center axis of the through-hole 43 is large, the Luer-lock portion 20 or the cap 30 makes contact with the tapered section 45. The Luer-lock portion 20 or the cap 30, after making contact with the tapered section 45, slides upward along the tapered surface of the tapered section 45, reducing the degree of shift between the center axis of the syringe 10 and the center axis of the through-hole. This prevents the Luer-lock portion 20 or the cap 30 from abutting the outer rim of the through-hole 43 of the syringe holding section 40. The syringe 10 can thus be pulled out without raising the syringe holding section 40.

Further, since the outer radius R2 of the large diameter section 32 of the cap 30 is larger than the outer radius R1 of the side peripheral section 11 of the syringe 10, a user can easily remove the cap 30 from the syringe 10 even for a syringe 10 with a small diameter and a small injection volume, for example, 0.5 or 1 ml.

An embodiment to which the present invention is applied is thus described above. The description and the drawings of the embodiment constituting a portion of the disclosure of the invention do not limit the scope of the invention.

An embodiment provided with a cap 30 as the attachment member has been described, but the attachment member may be provided as a different member that can be attached to the distal end portion of the syringe 10. For example, the member may be an injection needle holder for holding an injection needle.

An embodiment in which the support cylinder 42 projects from the top face of the base plate 41 has been described, but the support cylinder 42 may project upward and downward from the base plate 41.

TABLE 1

| Tapered Distance L Taper | 1 mm | | | | | 2 mm | | | | | 3 mm | | | | | 4 mm | | | | |
|---|---|---|---|---|---|---|---|---|---|---|---|---|---|---|---|---|---|---|---|---|
| Angle θ | 5° | 10° | 30° | 40° | 50° | 5° | 10° | 30° | 40° | 50° | 5° | 10° | 30° | 40° | 50° | 5° | 10° | 30° | 40° | 50° |
| Syringe Radius Difference 1 mm | O | O | O | O | X | O | O | O | O | X | O | O | O | O | X | O | O | O | O | X |
| Syringe Radius Difference 2 mm | X | X | X | X | X | O | O | O | X | X | O | O | O | X | X | O | O | O | X | X |
| Syringe Radius Difference 3 mm | X | X | X | X | X | X | X | X | X | X | X | X | X | X | X | X | X | X | X | X |

Table 1 shows the result of the experiment for the combinations of the cap 30 and the syringe holding section 40, where "X" indicates that the syringe holding section 40 has risen one or more times and "O" indicates that the syringe holding section 40 has never risen.

The result of the experiment shows that the preferable syringe radius difference is within a range from 1 to 2 mm. It shows that the tapered distance L is preferably larger than the syringe radius difference. If the syringe radius difference is 1 mm and the tapered distance L is within a range from 1 to 4 mm, the preferable taper angle θ is within a range from 5 to 40 degrees. If the syringe radius difference is 2 mm and the tapered distance L is within a range from 2 to 4 mm, the preferable taper angle θ is within a range from 5 to 30 degrees.

In the syringe container 1 of the embodiment, the inner peripheral surface 44 of the support cylinder 42 forming the through-hole 43 has the tapered section 45 from the bottom end to the approximately middle portion of the support cylinder 42 where the radius reduces as the tapered section 45 extends upward.

Provided in such a manner, when the syringe 10 attached with the cap 30 held in the syringe holding section 40 is to The support cylinder 42 may be formed to project downward from the bottom face of the base plate 41. In this case, the flange section 16 of the syringe 10 is supported by the upper end of the support cylinder 42 and the top face of the base plate 41.

The base plate 41 may be formed thick so that the through-hole 43 having the tapered section 45 is formed in the base plate 41 itself. In this case, the support cylinder 42 is omitted and the flange section 16 of the syringe 10 is supported by the top face of the base plate 41.

It should be noted that other embodiments, exemplary embodiments, arts for operation, or the like carried out based on the aforementioned embodiment by those skilled in the art should all fall within the scope of the present invention.

What is claimed is:
1. An assembly comprising:
   a cylindrical syringe including a distal end portion having a discharge opening for discharging a liquid, a proximal end portion arranged opposite the distal end portion, and a side peripheral section connected to the distal end portion and the proximal end portion;

an attachment member attached to the distal end portion and having an outer radius larger than an outer radius of the side peripheral section;

a container body including a bottom portion and a peripheral wall portion extending upward from a periphery of the bottom portion; and a syringe holding section configured to be placed within the container body, surrounded by the peripheral wall portion, so as to face the bottom portion, wherein the syringe holding section includes an inner peripheral surface that forms a through-hole, the syringe holding section configured to hold the syringe when the syringe is inserted in the through-hole, wherein the inner peripheral surface includes an upper end having a radius larger than an outer radius of the attachment member, a bottom end having a radius larger than the radius of the upper end of the inner peripheral surface, and a tapered section having a radius that tapers from a larger radius to a smaller radius as the tapered section extends upward from the bottom end of the inner peripheral surface, and wherein a difference between the radius of a bottom end of the tapered section and the radius of an upper end of the tapered section is equal to or larger than a difference between the outer radius of the attachment member and the outer radius of the side peripheral section.

2. The assembly according to claim 1, wherein the radius of the attachment member is 4.0 mm or larger.

3. The assembly according to claim 1, wherein an angle formed between a line parallel to the tapered section and a center axis of the through-hole is 5 to 40 degrees.

4. The assembly according to claim 1, wherein a Luer-lock portion configured to be connected to the attachment member is provided on the distal end portion of the syringe.

5. The assembly according to claim 1, wherein the assembly comprises a plurality of the cylindrical syringes.

6. The assembly according to claim 1, wherein the syringe holding section includes a plurality of inner peripheral surfaces that each form a through hole.

7. The assembly according to claim 1, wherein the tapered section extends no more than approximately half of the length of the inner peripheral surface.

8. The assembly according to claim 1, wherein the attachment member is a cap configured to plug the discharge opening of the syringe.

9. The assembly according to claim 1, wherein the syringe holding section includes a support cylinder and the syringe holding section is configured such that the inner peripheral surface that forms the through-hole is disposed in the support cylinder.

10. The assembly according to claim 9, wherein the assembly comprises a plurality of the support cylinders.

11. The assembly according to claim 9, wherein the tapered section extends no more than approximately half of the length of the support cylinder.

12. The assembly according to claim 9, wherein the tapered section has a linear taper shape.

13. The assembly according to claim 1,
wherein the peripheral wall portion comprises a ledge section, and
wherein the syringe holding section is configured to be placed within the container body, in contact with a top portion of the ledge section of the peripheral wall portion so that a base plate of the syringe holding section faces the bottom portion.

14. An assembly comprising:
a cylindrical syringe including a distal end portion having a discharge opening for discharging a liquid, a proximal end portion arranged on a side opposite the distal end portion, and a side peripheral section connected to the distal end portion and the proximal end portion;

an attachment member configured to be attached to the distal end portion and having an outer radius larger than an outer radius of the side peripheral section;

a container body including a bottom portion and a peripheral wall portion extending upward from a periphery of the bottom portion; and a syringe holding section configured to be placed within the container body, surrounded by the peripheral wall portion, so as to face the bottom portion, wherein the syringe holding section includes an inner peripheral surface that forms a through-hole, the syringe holding section configured to hold the syringe when the syringe is inserted in the through-hole, wherein, the inner peripheral surface includes an upper end having a radius larger than an outer radius of the attachment member, a bottom end having a radius larger than the radius of the upper end of the inner peripheral surface, and a tapered section having a radius that tapers from a larger radius to a smaller radius as the tapered section extends upward from the bottom end of the inner peripheral surface, wherein the syringe includes a flange section extending radially outward from the proximal end portion of the syringe, wherein the syringe holding section includes a support cylinder and the syringe holding section is configured such that the inner peripheral surface that forms the through-hole is disposed in the support cylinder, and wherein an outer radius of at least a portion of the flange section is larger than a inner radius of a upper end of the support cylinder.

15. An assembly comprising:
a cylindrical syringe including a distal end portion having a discharge opening for discharging a liquid, a proximal end portion arranged on a side opposite the distal end portion, and a side peripheral section connected to the distal end portion and the proximal end portion;

an attachment member configured to be attached to the distal end portion and having an outer radius larger than an outer radius of the side peripheral section;

a container body including a bottom portion and a peripheral wall portion extending upward from a periphery of the bottom portion; and a syringe holding section configured to be placed within the container body, surrounded by the peripheral wall portion, so as to face the bottom portion, wherein the syringe holding section includes an inner peripheral surface that forms a through-hole, the syringe holding section configured to hold the syringe when the syringe is inserted in the through-hole, wherein, the inner peripheral surface includes an upper end having a radius larger than an outer radius of the attachment member, a bottom end having a radius larger than the radius of the upper end of the inner peripheral surface, and a tapered section having a radius that tapers from a larger radius to a smaller radius as the tapered section extends upward from the bottom end of the inner peripheral surface, wherein the syringe holding section includes a support cylinder and the syringe holding section is configured such that the inner peripheral surface that forms the through-hole is disposed in the support cylinder, and wherein the tapered section extends from a bottom end of the support cylinder to the approximately middle portion of the support cylinder.

* * * * *